United States Patent [19]
Meyer

[11] 4,013,642
[45] Mar. 22, 1977

[54] HETEROCYCLIC COMPOUNDS CONTAINING SULPHO GROUPS

[75] Inventor: Hans Rudolf Meyer, Binningen, Switzerland

[73] Assignee: Ciba-Geigy Corporation, Ardsley, N.Y.

[22] Filed: June 10, 1975

[21] Appl. No.: 585,739

[30] Foreign Application Priority Data

June 12, 1974 Switzerland ............... 8031/74
June 12, 1974 Switzerland ............... 8033/74

[52] U.S. Cl. ............ 260/240 CA; 260/240 D; 252/301.22; 427/158
[51] Int. Cl.² ............................ C07D 307/78
[58] Field of Search .......... 260/240 CA, 240 D; 252/301.2 W, 301.22

[56] References Cited

UNITED STATES PATENTS

| | | |
|---|---|---|
| 3,627,758 | 12/1971 | Weber et al. ............ 260/240 D |
| 3,697,513 | 10/1972 | Siegrist ............ 260/240 D |
| 3,732,221 | 5/1973 | Siegrist et al. ............ 260/240 D |
| 3,833,510 | 9/1974 | Crounse et al. ............ 260/240 CA |

*Primary Examiner*—Arthur P. Demers
*Attorney, Agent, or Firm*—Joseph G. Kolodny; Edward McC. Roberts; Prabodh I. Almaula

[57] ABSTRACT

Heterocyclic compounds containing sulpho groups, a process for their preparation as well as a process for optically brightening organic materials on using said compounds are disclosed.

7 Claims, No Drawings

HETEROCYCLIC COMPOUNDS CONTAINING SULPHO GROUPS

The present invention relates to new heterocyclic compounds containing sulpho groups, a process for their manufacture and their use as optical brighteners for high-molecular organic materials.

The new heterocyclic compounds containing sulpho groups correspond to the formula

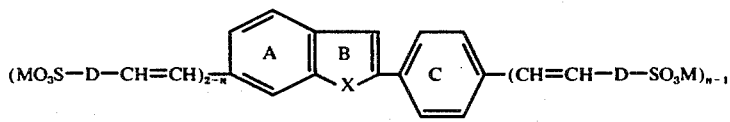

(1)

wherein the rings A, B and C are unsubstituted or have nonchromophoric substituents, X denotes oxygen or sulphur, M denotes hydrogen or a salt-forming cation, D denotes a phenylene, 4,4'-buphenylene or naphthylene radical which is unsubstituted or has non-chromophoric substituents, and $n$ denotes the number 1 or 2, it being possible, in the case where $n$ is the number 2, for two adjacent substituents on the ring A to form the completion of an indane or naphthalene ring which is unsubstituted or has non-chromophoric substituents.

Examples of non-chromphoric substituents are alkyl having 1 to 4 carbon atoms, cyclohexyl, α,α-dimethylbenzyl, benzyl, phenyl, fluorine, chlorine, bromine, alkoxy having 1 to 4 carbon atoms, benzyloxy, phenoxy, alkylmercapto having 1 to 4 carbon atoms, sulpho or, in the case of two adjacent substituents, also the 1,3-butadienylene, trimethylene or tetramethylene radical, the 1,3-butadienylene radical corresponding to a fused benzene ring.

Within the scope of the formula (1), emphasis should be given to the compounds of the formula tion denotes the trimethylene radical, $R_3$ denotes hydrogen or chlorine, and, if $n$ is the number 1, also denotes alkoxy having 1 to 4 carbon atoms, or 4-phenyl, $R_4$ denotes hydrogen or, if D denotes phenylene, also chlorine, alkyl having 1 to 4 carbon atoms, alkoxy having 1 to 4 carbon atoms, or sulpho or, conjointly with $R_5$ in the 3,4-position, denotes the tetramethylene or trimethylene radical, and $R_5$ denotes hydrogen or, if D denotes phenylene, also chlorine or alkoxy having 1 to 4 carbon atoms or, conjointly with $R_4$ in the 3,4-position, denotes the trimethylene or tetramethylene radical.

If D denotes a 4-biphenylene or naphthylene radical, $R_4$ and $R_5$ preferably represent hydrogen.

Methoxy is preferred in each case for "alkoxy having 1 to 4 carbon atoms". D preferably represents a phenylene radical and X in the formulae (1) and (2) preferably represents oxygen. "Sulpho" is to be understood as the radical $-SO_3M$ wherein M represents hydrogen or a salt-forming cation. Suitable salt-forming cations M are, in general, those of alkaline earth metals, for example of calcium, barium or magnesium, and, in particular, of alkali metals, for example of sodium or potassium, but also ammonium, optionally substituted by alkyl or hydroxyalkyl having 1 to 4 carbon atoms, or amine salt ions of cyclic amines, such as pyridine, morpholine and piperidine. Besides hydrogen, the potassium cation and the sodium cation, in particular, are preferred in the meaning of M.

Within the scope of the formula (2), interest attaches above all to both the compounds of the formula

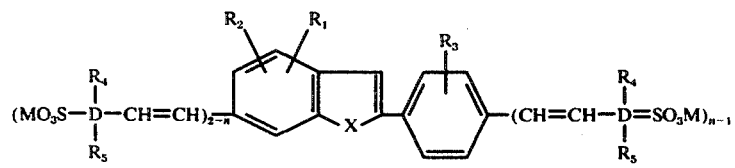

(2)

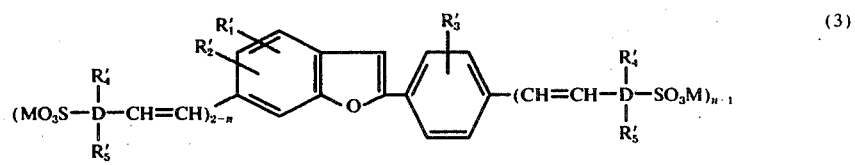

(3)

wherein D, M, X and $n$ have the abovementioned meaning, $R_1$ denotes hydrogen, chlorine, fluorine or, if $n$ is the number 2, also alkyl having 2 to 4 carbon atoms, alkoxy having 1 to 4 carbon atoms, cyclohexyl, phenyl, benzyl or α,α-dimethylbenzyl or, conjointly with $R_2$, in the o-position to one another, denotes the 1,3-butadienylene radical or in the 5,6-position denotes the trimethylene radical, $R_2$ denotes hydrogen or, if n is the number 2, also chlorine, alkyl having 2 to 4 carbon atoms or alkoxy having 1 to 4 carbon atoms, or, conjointly with $R_1$, in the o-position to one another, denotes the 1,3-butadienylene radical or in the 5,6-posiwherein D, M and $n$ have the meaning indicated above, $R'_1$ denotes hydrogen, chlorine or, if $n$ is the number 2, also alkoxy having 1 to 4 carbon atoms, cyclohexyl, phenyl, benzyl or α,α-dimethylbenzyl or, conjointly with $R'_2$, in the o-position to one another, denotes the 1,3-butadienylene radical or in the 5,6-position denotes the trimethylene radical, $R'_2$ denotes hydrogen or, if $n$ is the number 2, conjointly with $R'_1$, in the o-position to one another, denotes the 1,3-butadienylene radical or in the 5,6-position denotes the trimethylene radical, $R'_3$ denotes hydrogen and, if $n$ is the number 1, also chlorine, alkoxy having 1 to 4 carbon atoms, or 4-phenyl R'₄ denotes hydrogen or, if D denotes phenylene, also chlorine, alkyl having 1 to 4 carbon atoms, or alkoxy having 1 to 4 carbon atoms and R'₅ denotes hydrogen or, if D denotes phenylene, also alkoxy having 1 to 4 carbon atoms, and those of the formula

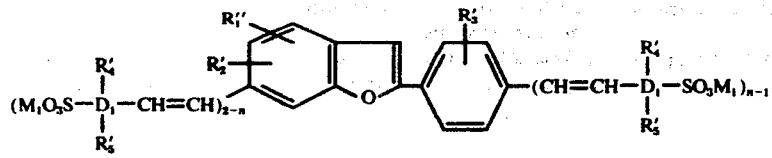

(4)

wherein R'₂, R'₃, R'₄, R'₅ and n have the meaning indicated above, R''₁ denotes hydrogen, chlorine or, if n is the number 2, also methoxy, cyclohexyl or phenyl or, conjointly with R'₂ in the 4,5-position or the 6,7-position, denotes the 1,3-butadienylene radical or in the 5,6-position denotes the trimethylene radical, D₁ denotes a phenylene radical or the 4,4'-biphenylene radical, and M₁ denotes a hydrogen ion, alkali metal ion, alkaline earth metal ion, ammonium ion or amine salt ion.

Particular practical interest attaches to the compounds of the formula

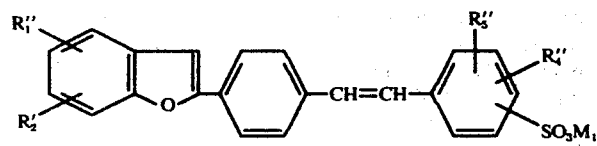

(5)

wherein R''₁, R'₂ and M₁ have the meaning indicated above, R''₄ denotes hydrogen, chlorine, methyl or methoxy, and R''₅ denotes hydrogen or methoxy, and of the formula

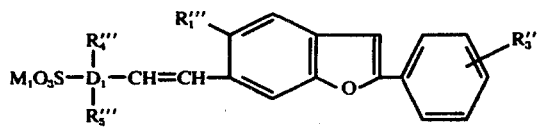

(6)

wherein D₁ and M₁ have the meaning indicated above, R'''₁ denotes hydrogen or chlorine, R'''₃ denotes hydrogen, chlorine, methoxy or, if D₁ is phenylene, also p-phenyl, R'''₄ denotes hydrogen or, if D₁ is phenylene, also chlorine, methyl or methoxy and R'''₅ denotes hydrogen or, if D₁ is phenylene, also methoxy.

The present invention also relates to a process for the manufacture of the new compounds of the formulae (1) to (6).

Various processes for the manufacture of heterocyclic compounds containing stilbene groups are already known. One such process, which is widely applicable, has been disclosed under the name "Anil Synthesis" [compare, for example, Helvetica Chimica Acta 50 (1967) 906 et. seq. and 52 (1969) 2521 et. seq.]. Hitherto, however, the absence from the reactants of substituents capable of salt formation, such as, for example, the sulphonic acid group, has been indicated as a condition for the progress of the anil synthesis [compare Helvetica Chimica Acta 50 (1967) 912 and 52 (1969) 2524].

It has now been found, surprisingly, that the 2-stilbenyl-benzofuranes, 6-styryl-benzofuranes, 2-stilbenyl-benzothiophenes and 6-styryl-benzothiophenes according to the invention, which contain sulpho groups, can also be manufactured in good yields by means of the anil synthesis. This process makes possible a particularly advantageous method of manufacturing these compounds.

The manufacture, according to the invention, of the compounds of the formula (1) is characterised in that a compound of the formula

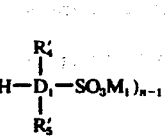

(7)

or (8)

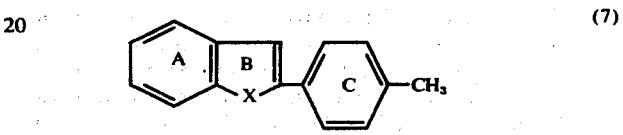

is reacted, in the presence of a strongly basic alkali metal compound in a, preferably strongly polar, neutral to basic organic solvent, with an anil of the formula $$Ar - N = CH - D - SO_3M \qquad (9)$$

wherein Ar denotes an unsubstituted or substituted aromatic radical.

The aromatic radical Ar is generally composed of one or more six-membered carbocyclic structures, and it preferably denotes an unsubstituted or substituted naphthyl or phenyl radical, particularly a phenyl radical which is unsubstituted or substituted by chlorine.

Correspondingly, the manufacture of the compounds of the formulae (2) to (6) is carried out by reacting compounds of the formulae

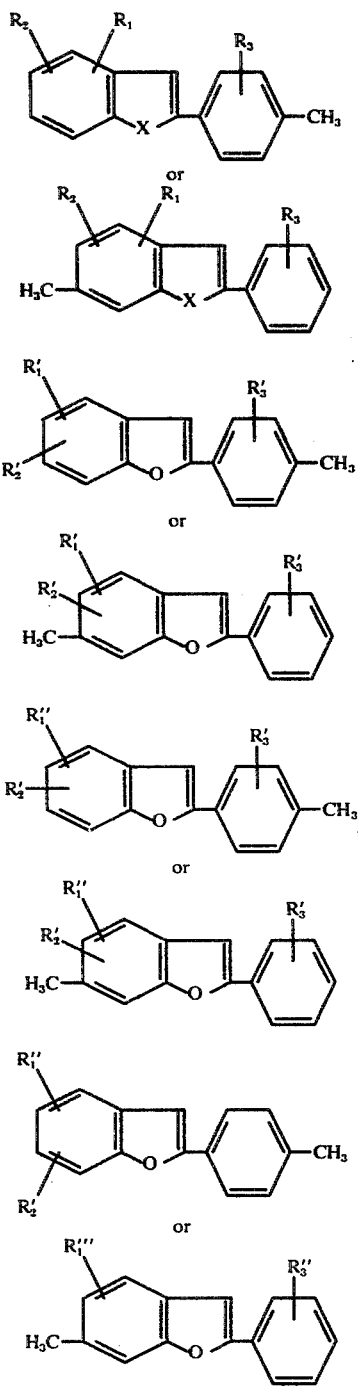

(10)
(11)
(12)
(13)
(14)
(15)
(16)
(17)

wherein the substituents have the meaning indicated earlier in the text, with the corresponding anils of the formulae

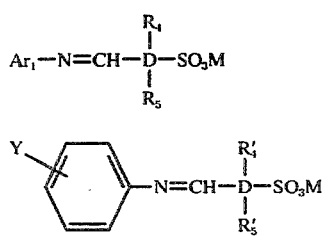

(18)
(19)

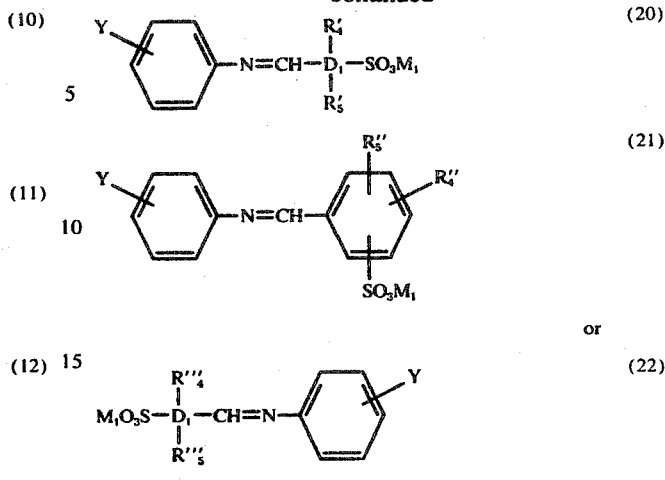

(20)
(21)
(22)

wherein the substituents have the meaning indicated earlier in the text.

The starting materials for the manufacture of the compounds of the formulae (1) to (6), that is to say the compounds of the formulae (7) to (22), are known or are manufactured in analogy to processes which are in themselves known.

The reaction with the anils can be carried out in the presence of a suitable, preferably strongly polar, neutral or alkaline organic solvent which is free from atoms, particularly hydrogen atoms, which can be replaced by alkali metals, In practice, possible solvents of this kind are, above all, dialkylamides of formic acid and of phosphoric acid and tetraalkylureas, "alkyl" denoting a lower alkyl group containing 1 to 4 carbon atoms, particularly a methyl group. The following should be mentioned as important representatives of such solvents: diethylformamide, hexamethylphosphoric acid triamide, tetramethylurea and, especially, dimethylformamide. Mixtures of solvents can also be used.

Furthermore, as mentioned, a strongly basic alkali metal compound is necessary for the reaction. Depending on the nature of the solvent used and the reactivity of the anil employed, certain sodium alcoholates, such as sodium t-butylate, and, particularly, potassium compounds of the composition $$KOC_{m-1}H_{2m-1}$$

wherein $m$ represents an integer from 1 to 6, preferably 2 to 6, such as, for example, potassium hydroxide or, particularly, potassium tert.-butylate, are suitable for this purpose. In the case of alkali metal alcoholates, the reaction must be carried out in a virtually anhydrous medium, while in the case of potassium hydroxide, a small water content of up to about 15% (for example contained as water of crystallisation) is still allowable. Potassium hydroxide or sodium t-butylate is sometimes used advantageously in combination with hexamethylphosphoric acid triamide at elevated temperature, for example at 110° to 130° C.

The compounds containing methyl groups are reacted with the anils in equivalent quantities. An excess of anil up to approx. 25% is, however, generally appropriate. It is advantageous to use at least an equivalent quantity of the alkali metal compound, that is to say at least 1 mol of a compound having, for example, a KO group, to one mol of anil. When potassium hydroxide is used, it is preferable to use a 4-fold to 8-fold quantity. Particularly good yields are obtained when employing K tert.-butylate in a quantity which is 1 to 6 times, preferably 2 to 4 times, the equivalent quantity.

The reaction according to the invention can generally be carried out at temperatures in the range between about 10° and 150° C. With particularly reactive anils, the reaction takes place even at room temperature, in which case no external supply of heat is necessary. This is particularly advantageous if the reactants contain ring compounds or substituents which are easily opened or split off, or modified chemically in some other way, by alkali. This is true, for example, for anils with chlorine substituents which can be split off easily. It is most advantageous, however, to carry out the reaction at elevated temperature, particularly when using sodium t-butylate or potassium hydroxide. For example, the reaction mixture is warmed slowly to 30° to 80° C and is then kept at this temperature for some time, for example ½ to 2 hours.

The manufacture of the anil and its reaction with the tolyl compound can also be carried out in a one-pot process. For example, an aldehyde is heated with an excess of aniline in dimethylformamide, the mixture is evaporated completely in vacuo, the tolyl component and dimethylformamide are added and the customary procedure is followed. The end products can be worked up from the reaction mixture by customary methods which are in themselves known. Isolation is carred out, for example, by precipitation with water or, in the case of water-soluble products, by salting out, for example using NaCl or KCl, or by neutralisation or, where appropriate, by acidification with a strong mineral acid, such as, for example, HCl, it being possible in this last case to liberate the free sulphonic acids, if desired. These can optionally be converted into the corresponding alkali metal salts, alkaline earth metal salts, ammonium salts or amine salts by reaction with alkali metal salts or alkaline earth metal salts or with ammonium hydroxide or amines. The amine salts of the sulphonic acids are also obtained, for example, by converting an alkali metal salt of the sulphonic acid into the sulphochloride by means of phosphorus oxychloride, thionyl chloride, phosphorus pentachloride and the like, and subsequent saponification in the presence of the desired amine.

The crude products are purified, as a rule, by extraction by boiling with chloroform and recrystallisation or extraction by boiling (depending on the solubility), for example with water, aqueous potassium chloride solution, n-propanol-water, ethylene glycol monomethyl ether, dimethylformamide, dimethylformamide-water, dimethylsulphoxide or dimethylsulphoxide-water.

The new compounds defined above exhibit a more or less pronounced fluoresence in the dissolved or finely dispersed state. They can be used for optically brightening the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high-molecular materials:

a. Polymerisation products based on organic compounds containing at least one polymerisable carbon-carbon double bond, that is to say their homopolymers or copolymers as well as their after-treatment products, such as, for example, crosslinking, grafting or degradation products, polymer blends or products obtained by modification of reactive groups, for example polymers based on $\alpha$, $\beta$-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride);

b. Polymerisation products which are obtainable by ring opening, for example, polyamides of the polycaprolactam type, and also polymers which are obtainable both via polyaddition and via polycondensation, such as polyethers or polyacetals;

c. Polycondensation products or precondensates based on bifunctional or polyfunctional compounds possessing condensable groups, their homocondensation and co-condensation products, and after-treatment products, such as, for example, polyesters, especially polyesters which are saturated (for example ethylene glycol terephthalic acid polyester) or unsaturated (for example maleic acid-dialcohol polycondensates as well as their crosslinking products with copolymerisable vinyl monomers), unbranched or branched (also including those based on polyhydric alcohols, such as, for example, alkyd resins), polyamides (for example hexamethylenediamine adipate), maleate resins, melamine resins, their precondensates and analogues, polycarbonates and silicones; and d. Polyaddition products such as polyurethanes (cross-linked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, that is to say for example, predominantly three-dimensional bodies such as slabs, profiles, injection mouldings, various machined articles, chips, granules or foams, and also as predominantly two-dimensional bodies such as films, sheets, lacquers, coverings, impregnations and coatings, or as predominantly one-dimensional bodies such as filaments, fibres, flocks and wires. The said materials can, on the other hand, also be in unshaped states, in the most diverse homogeneous or inhomogeneous forms of division, such as, for example, in the form of powders, solutions, emulsins, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the two before stretching.

The new optical brighteners according to the present invention can, for example, also be employed in the following use forms:

a. Mixed with dyestuffs (shading) of pigments (coloured pigments or especially, for example, white pigments), or as an additive to dye baths, printing pastes, discharge pastes or reserve pastes, and also for the after-treatment of dyeings, prints or discharge prints.

b. Mixed with so-called "carriers", wetting agents, plasticisers, swelling agents, anti-oxidants, light stabilisers, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or anti-microbial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches".

f. As additives to the most diverse industrial products in order to render these more marketable (for example improving the appearance of soaps, detergents and pigments), g. In combination with other optically brightening substances, h. In spinning bath preparations, that is to say as additives to spinning baths such as are used for improving the slip for the further processing of synthetic fibres, or from a special bath before stretching the fibre.

i. As scintillators for various purposes of a photographic nature, such as, for example, for electrophotographic reproduction or supersensitisation, and for the optical brightening of photographic layers, optionally in combination with white pigments, such as, for example, $TiO_2$.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention, is to impregnate these fibres with the aqueous dispersions (or optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brighteners are also particularly suitable for use as additives to wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brighteners can be mixed, kneaded or ground with the detergent substances and, in this form, admixed to the finished washing powder. However, they can also be sprayed in a dissolved or pre-dispersed form onto the finished washing agent.

Suitable washing agents are the known mixtures of detergent substances, such as, for example, soap in the form of chips and powders, synthetics, soluble salts of sulphuric acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali meal borates, alkali metal perborates, nitrilotriacetic acid, ethylenediaminetetraacetic acid, and foam stabilisers, such as alkanolamides of higher fatty acids. The washing agents can further contain, for example: antistatic agents, skin protection agents which restore fat, such as lanolin, enzymes, antimicrobial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The textiles quoted are treated for 1 to 30 minutes at 20° to 100° C in a wash liquor which contains 1 to 10 g/kg of a composite washing agent containing a builder and 0.05 to 1%, relative to the weight of washing agent, of the brighteners claimed. The liquor ratio can be 1:3 to 1:50.

After washing, rinsing and drying are carried out as usual. The wash liquor can contain 0.2 g/l of active chlorine (for example as hypochlorite) or 0.1 2 g/l of sodium perborate, as a bleaching additive.

In the examples, unless otherwise specified, percentages are always percentages by weight. Unless otherwise noted, melting points and boiling points are uncorrected.

EXAMPLE 1

20.3 g of potassium t-butylate are introduced into a solution of 6.25 g of 2-(p-tolyl)-benzofurane and 9.3 g of the sodium salt of o-benzaldehydesulphic acid anil in 50 ml of anhydrous dimethylformamide, whilst stirring vigorously and passing nitrogen over the mixture. The temperature is first kept at room temperature for ½ hour by gentle cooling and is then kept at 60° C for ½ hour and at 80° C for 1 hour, by warming. After cooling in an ice bath, 150 ml of water are added to the violet reaction mixture and the precipitated product is filtered off and washed with three times 20 ml of a 3% strength potassium chloride solution. Drying in vacuo at 100° C gives 12.5 g (about 97% of theory) of the compound of the formula

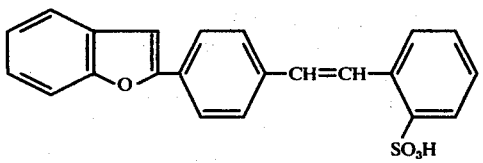
(101)

as the potassium salt, mixed with some sodium salt and having about ½ mol of water of crystallisation. This salt is recrystallised from about 300 ml of water with the aid of active charcoal and the addition of 3.5 g of potassium chloride after the mixture has been filtered hot. Yield 10.2 g of a pale yellow, hygroscopic powder.

The compound of the formula (101) is obtained similarly if the p-chloro anil of the formula

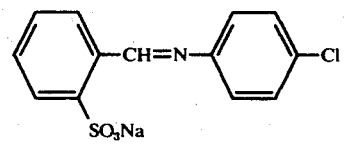

is employed as the anil component.

In order to prepare this compound, 223 g of the sodium salt of o-sulphobenzaldehyde in 480 g of p-chloroaniline are heated slowly, with stirring, to 185° C and the reaction mass, which has become liquid, is kept at this temperature for ½ hour. After cooling to approx. 130° C, 2 l of n-butanol are added and the mixture is filtered hot and allowed to cool to 0° C. The precipitate is filtered off, washed with twice 200 ml of n-butanol and dried in vacuo at 100° C. Yield 216 g, melting point approx. 239° C after recrystallisation from n-butanol. Further product can be additionally obtained by concentrating the mother liquor.

If, instead of 2-(p-tolyl)-benzofurane, the equivalent quantity of 2-(p-tolyl)-benzothiophene is used, the potassium/sodium salt of the compound of the formula

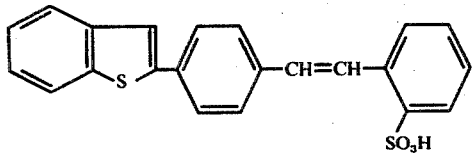
(102)

is obtained, which is recrystallised from aqueous alcohol.

The sodium salt of o-benzaldehydesulphonic acid anil is obtained as follows:

208 g of the crude sodium salt of o-sulphobenzaldehyde are boiled up briefly in 1,040 ml of ethylene glycol monomethyl ether and the solution is clarified by filtration at room temperature in order to remove insoluble salts. 93.1 g of freshly distilled aniline are added to the filtrate and the mixture is heated for 1 hour at reflux temperature and filtered again from precipitated salts. 300 ml are now first distilled off at atmospheric pressure and then the remainder of the solvent is distilled off under reduced pressure. The residue is crystallised from 1 liter of n-butanol, filtered off and dried at 100° C in vacuo. This gives 152 g of a colourless, hygroscopic product of the formula

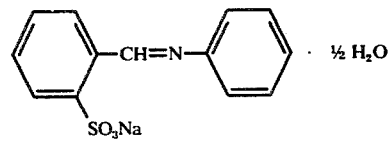
(103)

(after recrystallisation from n-butanol).

This anil is obtained in an even simpler manner by using, instead of ethylene glycol monomethyl ether, 1.21 of n-butanol, from which it crystallises out on cooling.

EXAMPLE 2

If, instead of the sodium salt of o-benzaldehyde-sulphonic acid anil, the same quantity of the sodium salt of m-benzaldehydesulphonic acid anil in 80 ml of dimethylformamide and 14.7 g of potassium t-butylate are used in Example 1, 11.55 g (about 92% of theory) of the compound of the formula (104)

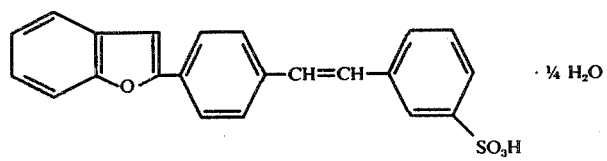

are obtained, after washing with water and drying, as a hygroscopic potassium salt. Purification is carried out by recrystallisation from dimethylformamide/water.

The potassium/sodium salt of the compound of the formula (105)

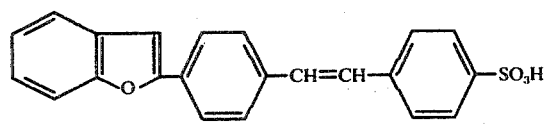

is obtained in an analogous manner, but using 350 ml of dimethylformamide (instead of 80 ml). The sodium salt of m-benzaldehydesulphonic acid anil is obtained according to the instructions for the o-derivative (Example 1). It is isolated by boiling up in alcohol (instead of n-butanol) the residue obtained after the distillation of the solvent and filtering off, at room temperature, the anil, which is insoluble therein, washing it with alcohol and drying.

The sodium salt of p-benzaldehydesulphonic acid anil is obtained as follows:

62.5 g of the crude sodium salt of p-sulphobenzaldehyde are briefly boiled up in 500 ml of dimethylformamide and the solution is clarified by filtration at room temperature in order to remove insoluble salts. 28 g of aniline are added to the filtrate and it is heated to the boil for 10 minutes, in the course of which the anil already crystallises out. 200 ml of solvent are distilled off, and mixture is cooled and filtered and the residue is washed with 50 ml of dimethylformamide and with twice 50 ml of methanol. This gives 51.3g of colourless crystals of the formula

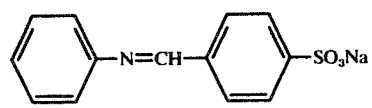
(106)

A further 7.4 g of product nearly as pure are obtained by concentrating the filtrate to about ⅓ of its original volume.

EXAMPLE 3

By following a procedure essentially in accordance with Example 1 or 2, using appropriate aldehyde anils and 2-(p-tolyl)-benzofurane derivatives and 3 mols of potassium t-butylate per mol of 2-(p-tolyl)-benzofurane derivative, the compounds of the general formula (107), listed in Table I, are obtained, mainly in the form of their potassium salts. The dimethylamine salts which are sometimes formed in part, can be converted into the potassium salts by boiling up in aqueous potassium carbonate or potassium hydroxide solution, the dimethylamine liberated being distilled off with water. In order to obtain the chlorine-containing compounds of the formulae (108) and (115), the reaction is carried out at room temperature. The initial purification is generally carried out by extraction by boiling with chloroform.

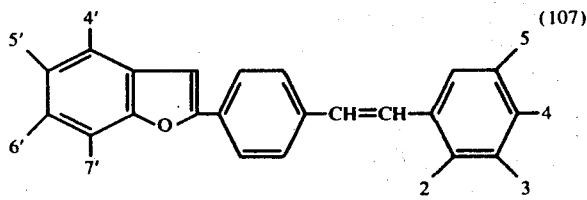

TABLE I

| Formula No. | substituents | |
|---|---|---|
| (108) | | 2-chloro 5-SO₃H |
| (109) | | 2,3-dimethoxy 5-SO₃H |
| (110) | | 2-methoxy 5-SO₃H |
| (111) | | 3-methyl 5-SO₃H |
| (112) | 5'-phenyl | 2-SO₃H |
| (113) | 5'-chloro | 2-SO₃H |
| (114) | 5'-cyclohexyl | 4-SO₃H |
| (115) | | 4-chloro 3-SO₃H |
| (116) | 5'-methoxy | 3-SO₃H |
| (117) | 4',5'-benzo | 3-SO₃H |
| (118) | 6',7'-benzo | 3-SO₃H |
| (119) | 5',6'-trimethylene | 2-SO₃H |
| (120) | 5'-chloro | 3-SO₃H |
| (121) | 5'-chloro | 4-SO₃H |
| (122) | 5'-phenyl | 3-SO₃H |
| (123) | 5'-phenyl | 4-SO₃H |
| (124) | 5'-cyclohexyl | 3-SO₃H |
| (125) | 5'-cyclohexyl | 2-SO₃H |

Anil components

The potassium salt of 2,3-dimethoxy-5-sulphobenzaldehyde anil, which is used as the starting product for the compound of the formula (109), is obtained by boiling 2,3-dimethoxy-5-sulphobenzaldehyde (K salt) with aniline (10% excess) in alcohol. The dilute solution is clarified by hot filtration, concentrated and cooled, whereupon the product crystallises.

The potassium salt of 3-methyl-5-sulphobenzaldehyde anil, which is required as the starting product for the compound of the formula (111), is obtained in an analogous manner from 3-methyl-5-sulphobenzaldehyde (K salt).

The sodium salt of 4-chloro-3-sulphobenzaldehyde anil, which is required as the starting product for the compound of the formula (115), is obtained in an analogous manner from 4-chloro-3-sulphobenzaldehyde (Na salt).

The sodium salt of 2-chloro-5-sulphobenzaldehyde anil, which is required for the compound of the formula (108) is obtained in accordance with the instructions for the potassium salt of m-benzaldehydesulphonic acid anil.

The sodium salt of 2-methoxy-5-sulphobenzaldehyde anil which is required for the compound of the formula (110), is obtained by boiling up 15.8 g of 2-methoxy-benzaldehyde-sulphonic acid (Na salt) in 100 ml of aniline and 23 ml of dimethylformamide, distilling off 30 ml of solvent and cooling.

The 2-(p-tolyl)-benzofurane derivatives and the 2-(p-tolyl)-benzothiophene derivatives are obtained in accordance with the instructions in Helvetica Chimica Acta 52 (1969) 1319–1322. 2-(pTolyl)5-cyclohexyl-benzofurane, which has not yet been described, melts at 154° C.

EXAMPLE 4

11.1 g of the potassium salt of biphenyl-4-aldehyde-4'-sulphonic acid, 89.2% strength, in 50 ml of aniline and 50 ml of dimethylformamide are stirred under reflux for ½ hour. The suspension is completely evaporated in vacuo at 130° C. 6.25 g of 2-(p-tolyl)-benzofurane and 100 ml of anhydrous dimethylformamide are added to the residue (anil), and 10.1 g of potassium t-butylate are introduced into the resulting suspension, while stirring and passing nitrogen over the mixture. The temperature is kept at 25° C for ½ hour, at 60° C for ½ hour and at 80° C for 1 hour, the mixture is cooled in an ice bath and 200 ml of desalinated water, are added. The precipitated product is filtered off, washed with water until neutral and dried. This gives 14.7 g (a quantitative yield) of the compound of the formula

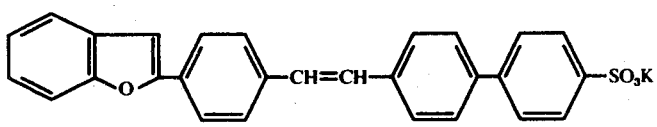

(126)

The compound of the formula

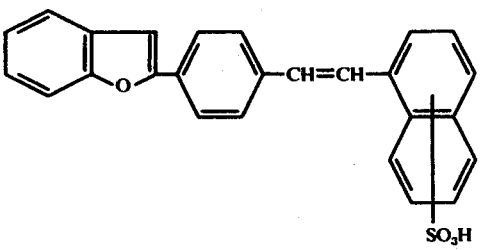

(127)

is obtained in an analogous manner as the potassium salt, mixed with some sodium salt, and is recrystallised from dimethylsulphoxide.

Biphenyl-4-aldehyde-4'-sulphonic acid (K salt) is obtained in good yield by introducing biphenyl-4-aldehyde into 25% strength oleum at 25 to 50° C, pouring the mixture out into ice and water and salting out by means of potassium chloride. 1-Naphthaldehydesulphonic acid is obtained by sulphonation of 1-naphthaldehyde.

EXAMPLE 5

14.5 g of the crude products of the formula (126) in 100 ml of phosphorus oxychloride are stirred under reflux for ½ hour. The suspension is cooled and filtered and the residue is washed with phosphorus oxychloride, acetone, water and again acetone and is dried in vacuo, first at 40° C and then at 80° C. After recrystallising from 400 ml of o-dichlorobenzene, using fuller's earth, 8.9 g of the sulphonic acid chloride are obtained as light yellow crystals (melting point >360° C). 8.3 g of this compound in 90 ml of dimethylformamide and 1 ml of water are heated under reflux for ½ hour. After cooling, the mixture is filtered and the residue is washed with dimethylformamide and alcohol and dried. This gives 8.5 g of a light yellow product of the formula

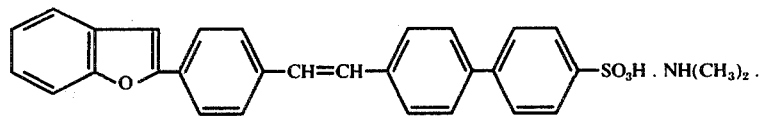
(128)

filtered off and washed repeatedly with water. Drying in vacuo at 100° C gives 14.0 g of the crude sulphonic acid of the formula

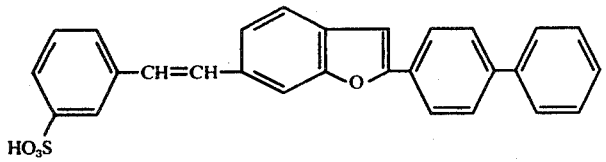
(129)

mainly as the potassium salt, which is extracted by boiling with 200 ml of chloroform and is recrystallised from 200 ml of dimethylsulphoxide.

7.4 g of this product in 70 ml of phosphorus oxychloride are heated under reflux for 1 hour. The cloudy solution is allowed to cool and the product which has crystallised out is filtered off and washed with benzene. After recrystallisation from chlorobenzene, with the aid of fuller's earth, 2.4 g are obtained of the sulphochloride of the formula

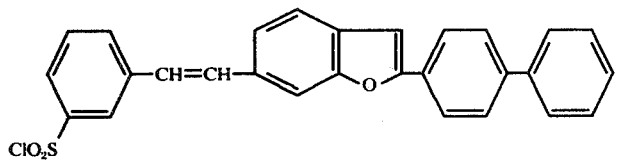

in the form of light yellow crystals of melting point 246° C.

2.2 g of this compound in 15 ml of pyridine and 0.2 ml of water are heated under reflux for ½ hour, and the reaction product is filtered off at room temperature, washed with pyridine and, repeatedly, with alcohol and dried in vacuo at 110° C. This gives 2.45 g of the sulphonic acid of the formula (129), mainly as the pyridinium salt of the formula

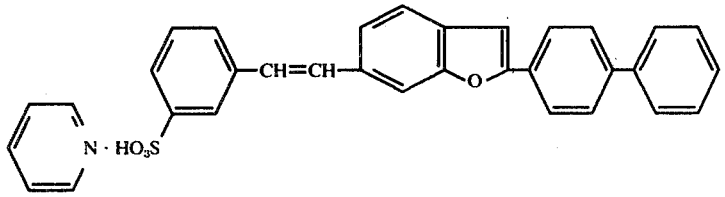
(130)

EXAMPLE 6

10.1 g of potassium t-butylate are introduced into a solution of 8.55 g of 2-(p-biphenylyl)-6-methylbenzofurane and 9.3 g of the sodium salt of m-benzaldehydesulphonic acid anil in 150 ml of anhydrous dimethylformamide, while stirring vigorously and passing nitrogen over the mixture. The temperature is allowed to rise to 80° C and the violet reaction mixture is stirred for 1 hour at 80° C. After cooling in an ice bath, 250 ml of water are added and the precipitated product is The products of the general formula (131), which are listed in Table II, are obtained in a similar manner to the compound off the formula (129), mainly in the form of their potassium salts. The p-sulphophenyl derivatives of the formulae (134) to (137) are prepared in accordance with Example 4.

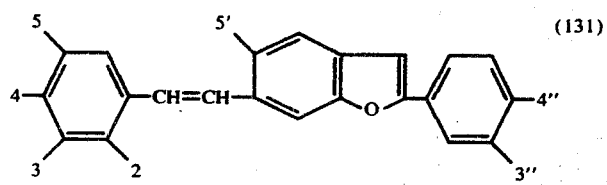

(131)

TABLE II

| Formula No. | Substituents | |
|---|---|---|
| (132) | 2—SO₃H | 4″-phenyl |
| (133) | 4—SO₃H | 4″-phenyl |
| (134) | 4—(C₆H₄)—SO₃H | |
| (135) | 4—(C₆H₄)—SO₃H | 4″-chloro |
| (136) | 4—(C₆H₄)—SO₃H | 3″-methoxy |
| (137) | 4—(C₆H₄)—SO₃H | 5′-chloro |
| (138) | 4—SO₃H | 4″-methoxy |

The 2-phenyl-6-methylbenzofurane derivatives of the general formula (140), which are required as starting products, are obtained, for example in accordance with Helvetica Chimica Acta 52 (1969) 1319–1322 via the m-cresol ethers of the general formula (139). Typical representatives are listed in Table III.

TABLE III

| (139) | Melting point °C | (140) | Melting point °C |
|---|---|---|---|
| CH₃—(C₆H₄)—O—CH₂—CO—(C₆H₄)—(C₆H₅) | 91 | CH₃—benzofuran—(C₆H₄)—(C₆H₅) | 217 |
| CH₃—(C₆H₄)—O—CH₂—CO—(C₆H₄)—Cl | 86 | CH₃—benzofuran—(C₆H₄)—Cl | 151 |
| CH₃—(C₆H₄)—O—CH₂—CO—(C₆H₄)—OCH₃ | 66 | CH₃—benzofuran—(C₆H₄)—OCH₃ | 56 |
| Cl,CH₃—(C₆H₃)—O—CH₂—CO—(C₆H₅) | 85 | Cl,CH₃—benzofuran—(C₆H₅) | 160 |

EXAMPLE 7

A polyamide fibre fabric (perlon-Helanca) is washed for 15 minutes, at a liquor ratio of 1:20, in a liquor warmed to 50 ° C which contains the following additives per liter:

0.004 to 0.016 g of a brightener of the formulae (101), (104), (108), (109), (110), (111), (112), or (130), 0.25 g of active chlorine (Javelle water) and 4 g of a washing powder of the following composition:
  15.00% of dodecylbenzenesulphonate,
  10.00% of sodium laurylsulphonate,
  40.00% of sodium tripolyphosphate,
  25.75% of anhydrous sodium sulphate,
  7.00% of sodium metasilicate,
  2.00% of carboxymethylcellulose and
  0.25% of ethylenediaminetetraacetic acid.

The polyamide fibre fabric is not introduced into the wash liquor, warmed to 50° C, until 15 minutes after the preparation of the latter. After rinsing and drying, the fabric exhibits a good brightening effect.

The washing powder of the abovementioned composition can also contain the brightener of the formulae designated above, directly incorporated.

EXAMPLE 8

Bleached cotton material is washed for 15 minutes, at a liquor ratio of 1:20, in a liquor warmed to 50° C which contains the following additives per liter:

0.004 g of a brightener of the formulae (101),(104), (109), (110), (112) or (113), 0.25 g of active chlorine (Javelle water) and 4 g of a washing powder of the following composition:
  15.00% of dodecylbenzenesulphonate,
  10.00% of sodium laurylsulphonate,
  40.00% of sodium tripolyphosphate,
  25.75% of anhydrous sodium sulphate,
  7.00% of sodium metasilicate,
  2.00% of carboxymethylcellulose and
  0.25% of ethylenediaminetetraacetic acid.

The cotton material is not introduced into the wash liquor, warmed to 50° C, until 15 minutes ater the preparation of the bath. After rinsing and drying, the fabric exhibits a good brightening effect with good fastness to chlorine.

The washing powder of the abovementioned composition can also contain these brighteners directly incorporated.

EXAMPLE 9

A polyamide fibre fabric (Perlon) is introduced, at a liquor ratio of 1:40 and at 60° C, into a bath which contains (relative to the weight of material) 0.05% of a brightener of the formulae (101), (104), (108), (109), (110), (111), (112), (114), (128) (130), (132) or (134) and, per liter, 1 g of 80% strength acetic acid and 0.25 g of an addition reaction product of 30 to 35 mols of ethylene oxide with one mol of technical grade stearyl alcohol. The bath is warmed to the boil over the course of 30 minutes and is kept at the boil for 30 minutes. After rinsing and drying, a good brightening effect is obtained.

Similar brightening effects are obtained if, instead of the fabric of polyamide 6, a fabric of polyamide 66 (nylon) is used.

Finally, it is also possible to work under high temperature conditions, for example for 30 minutes at 130° C. The addition of 3 g/l of hydrosulphite is advisable for this method of application.

EXAMPLE 10

10,000 g of a polyamide prepared in a known manner from hexamethylenediamine adipate are mixed, in the form of chips, in a tumbler for 12 hours with 30 g of titanium dioxide (rutile modification) and 5 g of a compound of the formula (108), (111), (127), (128), (130) or (134). The chips treated in this way are melted, after displacing the atmospheric oxygen by steam, in a kettle heated to 300° to 310° C by means of oil or diphenyl vapour, and are stirred for half an hour. The melt is then extruded through a spinneret under a nitrogen pressure of 5 atmospheres gauge, and the filament spun in this manner is cooled and wound up on a spinning bobbin. The resulting filaments exhibit a good brightening effect.

Similarly good results are obtained if, instead of a polyamide prepared from hexamethylenediamine adipate, a polyamide prepared from ε-caprolactam is used.

EXAMPLE 11

Bleached cotton material is washed for 30 minutes at 95° C at a liquor ratio of 1:20. The wash liquor contains the following additives per liter:
0.004 g of a brightener of the formulae (101), (104), (109), (110), (112) or (113) and 4 g of a washing powder of the following composition:
40.0% of soap flakes,
15.0% of sodium tripolyphosphate,
8.0% of sodium perborate,
1.0% of magnesium silicate,
11.0% of sodium metasilicate (9 $H_2O$),
24.6% of calcined sodium carbonate and
0.4% of ethylenediaminetetraacetic acid.

After rinsing and drying, the cotton fabric exhibits a good brightening effect with good fastness to chlorine.

EXAMPLE 12

An article of cotton material, finished in a non-iron manner by means of aminoplast resin, is washed, at a liquor ratio 1:20, for 15 minutes in a liquor warmed to 55° C which contains the following additives per liter:
0.004 to 0.016 g of a brightener of the formulae (101), (104), (109), (110) or (113) and 4 g of a washing powder of the following composition:
15.00% of dodecylbenzenesulphonate,
10.00% of sodium laurylsulphonate,
40.00% of sodium tripolyphosphate,
25.75% of anhydrous sodium sulphate,
7.00% of sodium metasilicate,
2.00% of carboxymethylcellulose and
0.25% of ethylenediaminetetraacetic acid.

After rinsing and drying, the fabric exhibits a strong brightening effect with good fastness to light.

EXAMPLE 13

A casting composition consisting of 10 g of polyacrylonitrile, 0.2 g of titanium dioxide (anatase modification) as delustring agent and 40 ml of dimethylformamide, and containing 5 mg of one of the compounds of the formulae (108), (127), (130) or (134), is cast on a glass sheet and drawn out into a thin film by means of a metal rod.

After drying, the film is strongly brightened.

What is claim is:

1. A heterocyclic compound containing sulpho groups of the formula

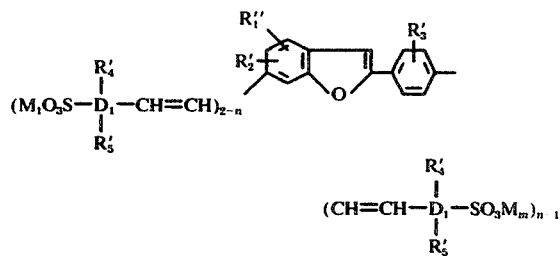

wherein
$n$ denotes the number 1 or 2,
$R'_2$ denotes hydrogen or, if $n$ is the number 2, conjointly with $R''_1$, in the 4,5-position or the 6,7-position, denotes 1,3-butadienylene or in the 5,6-position denotes trimethylene;
$R'_3$ denotes hydrogen and, if $n$ is the number 1, also chloro, alkoxy of 1 to 4 carbon atoms or 4-phenyl;
$R'_4$ denotes hydrogen or, if $D_1$ denotes phenylene, also chloro, alkyl of 1 to 4 carbon atoms or alkoxy of 1 to 4 carbon atoms;
$R'_5$ denotes hydrogen or, if $D_1$ denotes phenylene, also alkoxy of 1 to 4 carbon atoms;
$R''_1$ denotes hydrogen, chloro or, if $n$ is the number 2, also methoxy, cyclohexyl or phenyl or, conjointly with $R'_2$ in the 4,5-position on the 6,7-position, denotes said 1,3-butadienylene or in the 5,6-position denotes said trimethylene;
$D_1$ denotes phenylene or 4,4'-biphenylene; and
$M_1$ denotes a hydrogen ion, alkali metal ion, alkaline earth metal ion, ammonium ion or amine salt ion.

2. A heterocyclic compound containing sulpho groups, according to claim 1, of the formula

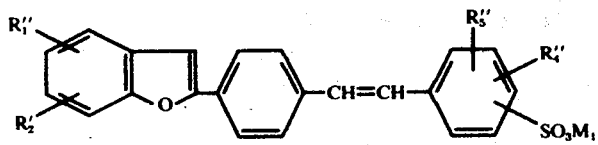

(5)

wherein $R''_1$, $R'_2$ and $M_1$ have the meaning indicated in claim 1, $R'''_4$ denotes hydrogen, chlorine, methyl or methoxy and $R''_5$ denotes hydrogen or methoxy.

3. A heterocyclic compound containing sulpho groups, according to claim 1, of the formula

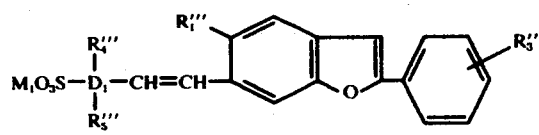

wherein $D_1$ and $M_1$ have the meaning indicated in claim 1, $R'''_1$ denotes hydrogen or chlorine, $R'''_3$ denotes hydrogen, chlorine, methoxy or, if $D_1$ is phenylene, also p-phenyl, $R'''_4$ denotes hydrogen or, if $D_1$ is phenylene, also chlorine, methyl or methoxy and $R'''_5$ denotes hydrogen or, if $D_1$ is phenylene, also methoxy.

4. A heterocyclic compound according to claim 1 of the formula

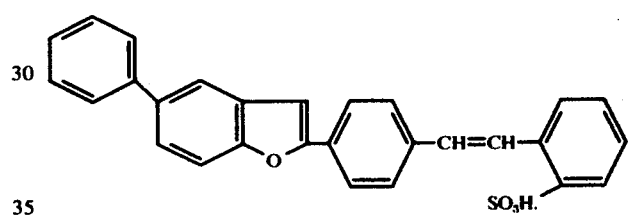

(6)

5. A heterocyclic compound according to claim 1 of the formula

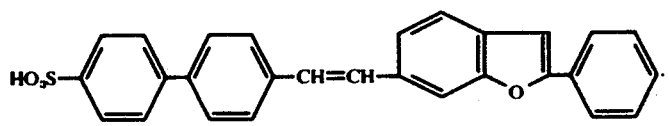

6. A heterocyclic compound according to claim 1 of the formula

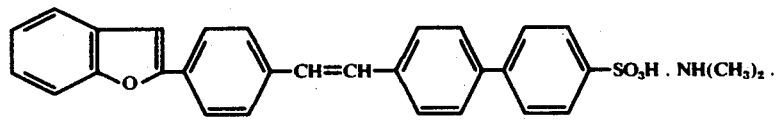

7. A heterocyclic compound according to claim 1 of the formula (128)

* * * * *